US005253486A

United States Patent [19]

Sugahara et al.

[11] Patent Number: 5,253,486

[45] Date of Patent: Oct. 19, 1993

[54] SILENCER ATTENUATING A NOISE FROM A NOISE SOURCE TO BE VENTILATED AND A METHOD FOR ACTIVE CONTROL OF ITS NOISE ATTENUATION SYSTEM

[76] Inventors: Masanori Sugahara; Keiji Nakanishi; Yasuyuki Sekiguchi, all of c/o Intellectual Property Division, Toshiba Corporation, 1-1, Shibaura 1-Chome, Minato-Ku, Tokyo, Japan

[21] Appl. No.: 692,359

[22] Filed: Apr. 26, 1991

[30] Foreign Application Priority Data

May 1, 1990 [JP] Japan .......................... 2-116259

[51] Int. Cl.[5] .......................... F01N 1/06; A61F 11/06

[52] U.S. Cl. .......................... 62/296; 181/206; 381/71; 417/312

[58] Field of Search .......................... 62/296, 115; 181/202, 181/200, 206; 381/71, 73.1, 94; 417/14, 312

[56] References Cited

U.S. PATENT DOCUMENTS

| | | | |
|---|---|---|---|
| 3,612,213 | 10/1971 | Piko | 417/312 X |
| 4,025,724 | 5/1977 | Davidson, Jr. et al. | 181/206 X |
| 4,044,203 | 8/1977 | Swinbanks | 181/206 X |
| 4,527,282 | 7/1985 | Chaplin et al. | 381/71 |
| 5,010,739 | 4/1991 | Isshiki | 62/296 X |

FOREIGN PATENT DOCUMENTS

| | | | |
|---|---|---|---|
| 0005696 | 11/1988 | Japan | 381/71 |
| 2223376A | 4/1990 | United Kingdom . | |

*Primary Examiner*—William E. Wayner

*Attorney, Agent, or Firm*—Limbach & Limbach

[57] ABSTRACT

A silencer attenuating a noise from a noise source to be ventilated of this invention comprises a machine compartment with a one-dimensional duct configuration whose sectional dimension is sufficiently small in comparison with the wavelength of the noise to be attenuated, a compressor and/or other machinery disposed within the machine compartment, an opening for dissipation of heat as disposed in a wall of the machine compartment and opening in a direction generally perpendicular to the direction of advance of sound within the machine compartment, a vibration pickup for detecting the vibration of the machinery corresponding to the output noise of the machinery, and a control circuit for processing output signals from the vibration pickup to drive a sound generator such as a speaker. The sound generator outputs a controlling signal dependent on the machine noise to cancel the noise about to emerge from the machine compartment.

14 Claims, 16 Drawing Sheets

SILENCER ATTENUATING A NOISE FROM A NOISE SOURCE TO BE VENTILATED AND A METHOD FOR ACTIVE CONTROL OF ITS NOISE ATTENUATION SYSTEM

BACKGROUND OF THE INVENTION a. Technical Field of the Invention

The present invention relates to a silencer having a noise control system employing the principle of active attenuation.

b. Prior Art Technology

There has already been proposed a noise control system employing the principle of active attenuation. (U.S. Pat. No. 4,527,282). This method is implemented in such a manner that vibrations from a driver or noise-killing speaker are introduced into a acoustically partially closed volume whose largest dimension is several times smaller than the wavelength of the highest frequency of the vibrations which are the object of noise cancellation and a microphone is disposed in said volume to stabilize the sound pressure in the neighborhood of the microphone, whereby the frequency range over which noise cancellation is effective is expanded.

A noise attenuation system of this type can be utilized for cancelling the noise of the machinery disposed within a machine chamber having an opening for heat dissipation. As a typical example of machinery installed in a machine chamber having an opening for heat dissipation is a refrigerator compressor.

The application of this concept of active attenuation of noise to a refrigerator is now described with reference to the schematic diagram presented in Fig. 23.

Disposed in the machine compartment 10 in the lowermost position at the back of a refrigerator is a compressor 20 which is a principal source of refrigerator noise. This machine compartment 10 is hermetically closed except at an opening or opening 17 available for dissipation of heat and water vapor due to defrosting and has a one-dimensional duct structure. That is to say, compared with the wavelength of compressor noise S to be reduced, the sectional dimension of the duct is made sufficiently small so that the compressor noise within the machine compartment 10 will be a one-dimensional plane progressive wave. The compressor noise S is detected by a microphone 35 disposed within the machine compartment 10 and far away from the opening 17. The compressor noise detected by the microphone 35, that is the detected sound M, is processed by a control circuit 40 with a transfer function G which, for example, has a finite impulse response filter (hereinafter referred to as FIR filter) which processes signals in the time domain as such, and, then, is fed to a speaker 50. The controlling sound A from this speaker 50 cancels the compressor noise which would otherwise emerge unattenuated from the machine compartment opening 17.

The transfer function G of the control circuit 40 is determined as follows.

First, the sound M detected by the microphone 35 can be expressed by means of the following equation (1)

$$M = S \times G_{SM} + A \times G_{AM} \tag{1}$$

where S is the noise produced by the compressor 20, A is the controlling sound output of the speaker 50, $G_{SM}$ is the acoustic transfer function between the compressor and the microphone, and $G_{AM}$ is the acoustic transfer function between the speaker and the microphone.

Provided that a microphone 55 for the evaluation of noise-attenuating effect is installed at the machine compartment opening 17, the measured sound R at this evaluation microphone 55 can be expressed using the following equation (2)

$$R = S \times G_{SR} + A \times G_{AR} \tag{2}$$

where $G_{SR}$ is the acoustic transfer function between the compressor and the opening and $G_{AR}$ is the acoustic transfer function between the speaker and the opening.

Since G is the transfer function between the microphone and the speaker, the following equation (3) holds.

$$A = M \times G \tag{3}$$

Now, in order that the compressor noise that would emerge from the opening 17 may be cancelled, the following equation should hold true.

$$R = 0 \tag{4}$$

From the above equations (1) through (4), the transfer function G for noise cancellation is expressed by the following equation (5).

$$G = G_{SR}/(G_{SR} \times G_{AM} - G_{SM} \times G_{AR}) \tag{5}$$

Dividing the denominator and numerator of the above equation (5) by $G_{SM}$ gives the following equation (6), provided that $G_{MR}$ is defined by equation (7).

$$G = G_{MR}/(G_{MR} \times G_{AM} - G_{AR}) \tag{6}$$

$$G_{MR} = G_{SR}/G_{SM} \tag{7}$$

By using these equations (6) and (7), the transfer function G necessary for the measured sound R to be 0 can be found by measuring the transfer function ratio $G_{MR}$ of $G_{SR}$ to $G_{SM}$ even if the compressor sound S is unknown. Thus, all that is necessary is to input the detected sound M to produce a measured sound R as a response while the compressor 20 is allowed to produce noise S.

By applying the transfer function G determined in the above manner to the control circuit 40, a controlling sound A corresponding to compressor noise S can be generated to thereby cancel the noise S at the machine compartment opening 17.

In applying the above active attenuation method, the schema of detecting compressor noise S by the microphone 35 presents the following problems.

The first problem is that the microphone 35 receives not only the noise S of compressor 20 but also the controlling sound A from the speaker 50. This can lead to positive acoustic feedback, or howling. This means that the output of the speaker 50 cannot be raised to a sufficiently high level to obtain the desired noise-reducing effect. This problem can be solved by interposing an echo canceller for prevention of howling in the control circuit 40 but the practice results in added cost.

Furthermore, in case a cooling fan for the compressor 20 is installed within the machine compartment 10, the microphone 35 picks up the noise from the fan as well, thus complicating the noise control system. Furthermore, there is a constant risk for the noise reduction system responding to external noise.

OBJECTS OF THE INVENTION

The object of the present invention is to provide a noise control system according to the principle of active attenuation which controls the noise of a noise source to be ventilated such as the compressor in the refrigerator, which precludes howling and is free from interferences due to sounds other than machine noise.

SUMMARY OF THE INVENTION

A silencer attenuating noise from a noise source requiring ventilation according to claim 1, which is appended hereto, comprises a machine compartment of one-dimensional duct structure having a sufficiently reduced sectional dimension with respect to the wavelength of the noise to be cancelled, machinery such as a compressor which is disposed in said machine compartment and can be a source of noise, an opening for dissipation of heat in a wall of said machine compartment which lies in a direction generally perpendicular to the direction of advance of sound within the machine compartment, a vibration pickup, attached to the machinery, and adapted to sense vibrations of the machinery acting as a source of noise, a control circuit for processing output signals from said vibration pickup, and a sound generator such as a speaker which is driven by output signals from said control circuit to produce a controlling sound in the machine compartment.

The aforesaid vibration pickup detects the machine vibrations corresponding to the noise produced by the compressor or/and other machinery. The control circuit processes the output signal from this vibration pickup and drives the sound generator such as a speaker, whereupon the sound generator produces a controlling sound corresponding to the machine noise. In this manner, the machine noise which is to emerge from the machine compartment opening is cancelled by the controlling sound.

In the above arrangement, even if the output level of the noise-killing sound generator is increased, there is no risk of howling due to the controlling sound, nor are there interferences from sounds other than the sound of the machinery on which the vibration pickup is disposed, for example the sound of the compressor cooling fan and the sound from external sources.

A silencer claimed in claim 2 is a modification of a silencer of claim 1, wherein the noise source is a compressor constituting a refrigerating cycle.

A silencer claimed in claim 3 is different from a silencer of claim 2 in that a vibration pickup 30 disposed on a portion of a suction pipe 24 proximate to the compressor 20 is used to pickup the vibrations of the compressor. In this arrangement, the thermal degradation of the vibration pickup 30 is precluded and, hence, the erratic action of the noise cancelling system is inhibited.

A silencer claimed in claim 4 is a modification of a silencer of claim 2, wherein the compressor, which is a source of noise, is installed in the farthest position away from said opening, so that more time can be allotted to signal processing in the control circuit.

A silencer according to claim 5 is a modification of a silencer of claim 2 wherein vibrations pickup is mounted on the compressor body. The vibration pickup preferably picks up vibrations tangential to the compressor body. In this embodiment, the sound of rotation of a rotary compressor can be detected with improved sensitivity.

A silencer according to claim 6 is such that, in a silencer of claim 2, said vibration pickup is installed on a motor of said compressor which is a source of noise. In this case, just as in the case where the vibration pickup is installed on the compression body, the noise is effectively cancelled by the controlling sound.

A silencer of claim 7 is such that, in a silencer claim in claim 6, the vibration pickup is mounted on the end face of the motor, whereby the installation of the vibration pickup is rendered easier and more secure, thus reducing chances of misinstallation.

A silencer attenuating a noise from a noise source to be ventilated of claim 8 includes two openings for dissipation of heat which open at both ends of a wall of its machine compartment in a direction generally perpendicular to the direction of advance of the sound within the machine compartment and machinery, such as a compressor, as a source of noise and a sound generator such as a speaker which produces a controlling sound in a central zone of the machine compartment. In this arrangement, the transfer function between the compressor and each opening and that between the speaker and each opening can be made equal so that one sound-cancelling system may take care of two openings. This arrangement insures a sufficient dissipation of heat from the compressor.

A silencer of claim 9 is such that, in a silencer of claim 8, a vibration pickup is used as a means for picking up sound source signals so that interferences from the noise of the cooling fan for the compressor and the external sound are eliminated.

The active attenuation principle embodied in the sound-reducing system in a silencer of claim 10 includes a device in the control circuit that applies the transfer factor G for noise cancellation to cause the sound generator to output a controlling sound corresponding to the noise of the compressor and other machinery which is a source of noise to cancel the machine noise which is to emerge from the machine compartment opening.

The active control method employed in the noise reducing system in a silencer according to claim 11 is such that the transfer factor G is defined by:

$$G = -G_{MR}/G_{AR}$$

$$G_{MR} = G_{SR}/G_{SM}$$

Where $G_{SR}$ is the acoustic transfer function between the compressor and the opening; $G_{AR}$ is the acoustic transfer function between the speaker and the opening; and $G_{SM}$ is the transmission function between the compressor and the vibration pickup.

In this arrangement, the transfer function G for the control circuit can be found by measuring the transfer function ratio $G_{MR}$ even if the compressor noise level is unknown.

BRIEF DESCRIPTION OF THE DRAWINGS

FIGS. 1 through 4 illustrate a first embodiment of the invention, in which:

FIG. 1 is a disassembled perspective view showing the lowermost part at the back of the low-noise refrigerator;

FIG. 2 is a schematic view showing the active control noise-attenuation system shown in FIG. 1;

FIG. 3 is a diagram showing the coherence functions between the vibration in the direction of the X-axis of the compressor as measured at the mounting position of the vibration pickup shown in FIG. 1 and the compressor noise;

FIG. 4 is a diagram showing the coherence function between the vibration in the direction of the Z-axis of the compressor as measured at the mounting position of the vibration pickup shown in FIG. 1 and the compressor noise;

FIGS. 5 through 7 illustrate a second embodiment, in which:

FIG. 5 is a disassembled perspective view showing the lowermost part at the back of the low-noise refrigerator;

FIG. 6 is a diagram showing the coherence function between the compressor vibration measured at the mounting position of the vibration pickup shown in FIG. 5 and the compressor noise;

FIG. 7 is a diagram showing the coherence function between the vibration measured at a different position on the circumferential surface of the motor driving the compressor and the compressor noise;

FIGS. 8 through 14 illustrate a third embodiment, in which:

FIG. 8 is a disassembled perspective view showing the lowermost part at the back of the low-noise refrigerator;

FIG. 9 is a diagram showing an example of transfer function G for noise attenuation to be applied to the control circuit;

FIG. 10 is a diagram showing the coherence function between the vibration in the tangential direction of the compressor body as measured at the mounting position of the vibration pickup and the compressor noise;

FIG. 11 is a noise level diagram showing the noise attenuation effect of the low-noise refrigerator illustrated in FIG. 8;

FIG. 12 is a diagram showing the coherence function between the vibration in the direction normal to the compressor body and the compressor noise;

FIG. 13 is a diagram showing an example of transfer function G for noise attenuation to be applied to the control circuit in the embodiment illustrated in FIG. 12;

FIG. 14 is a noise level diagram showing the noise attenuation effect of the refrigerator in case the transfer function of FIG. 13 is applied to the control circuit;

FIGS. 15 through 17 illustrate a fourth embodiment, in which:

FIG. 15 is a diagram showing the coherence function between the compressor vibration measured at the mounting position of the vibration pickup and the compressor noise;

FIG. 16 is a diagram showing the coherence function obtained with a vibration pickup mounted in a position different from that shown in FIG. 5;

FIG. 17 is a diagram showing the coherence function between the vibration measured at a still another position and the compressor noise;

FIGS. 18 through 20 illustrate a fifth embodiment, in which:

FIG. 18 is a compressor side elevation view showing the mounting position of the vibration pickup in the low-noise refrigerator;

FIG. 19 is a diagram showing the coherence function between the compressor vibration in the direction of X-axis as measured at the mounting position of the vibration pickup shown in FIG. 18 and the compressor noise;

FIG. 20 is a diagram showing the coherence function between the vibration in the direction of Y-axis as measured on the circumferential surface of the motor driving the compressor and the compressor noise;

DETAILED DESCRIPTION OF THE PREFERRED EMBODIMENTS

The following detailed description pertains to the application of the invention to a refrigerator.

The first embodiment of the present invention will now be described below, referring to FIGS. 1 through 4.

Figure 1:
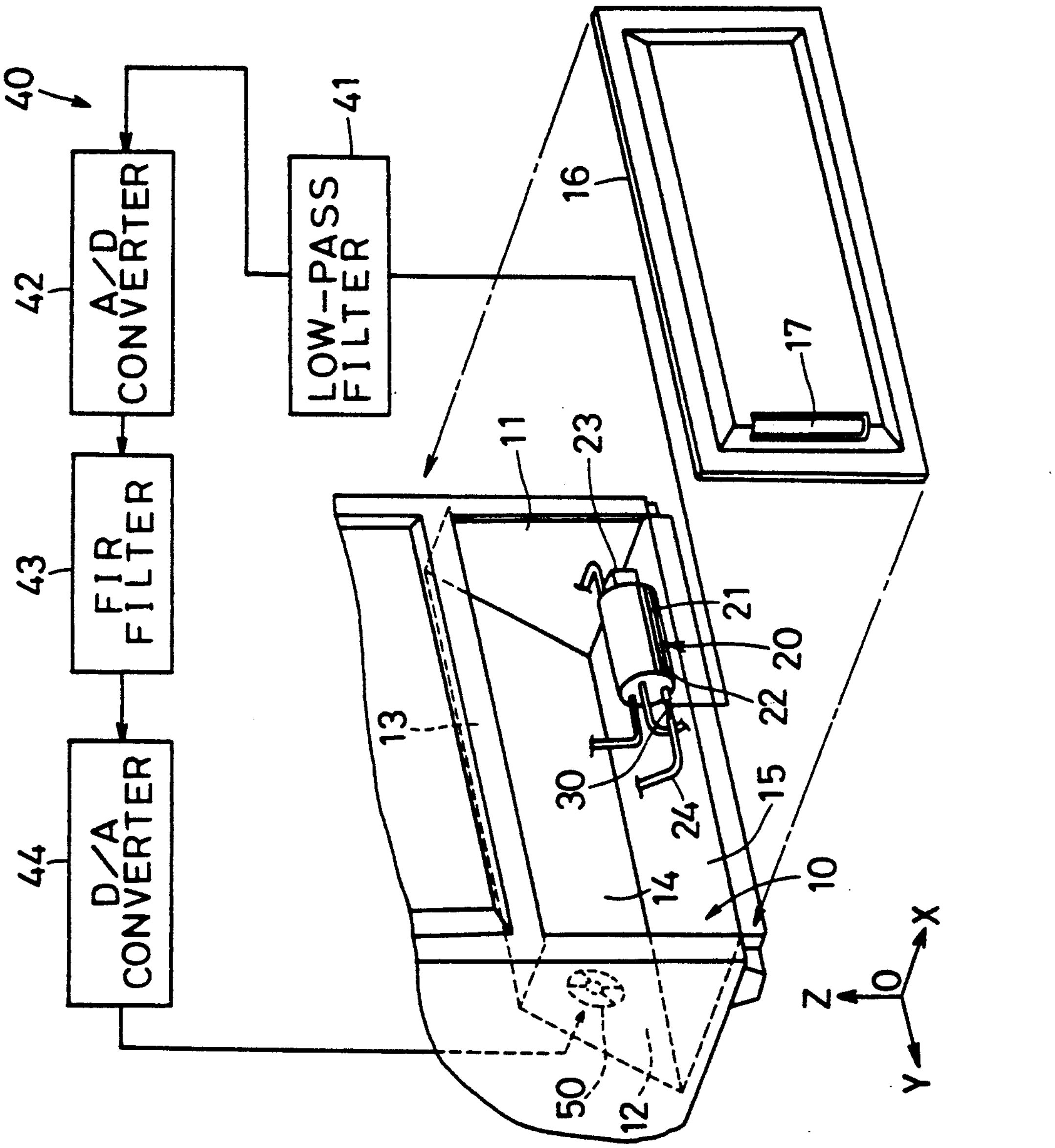

FIG. 1 is a disassembled perspective view showing the lowermost part at the back of a low-noise refrigerator according to the present invention.

The reference numeral 10 indicates a machine compartment disposed at the lowermost part of the back of the refrigerator. This machine compartment 10 is acoustically closed by two lateral plates 11, 12, a ceiling plate 13, a front inclined plate 14, a bottom plate 15 and a back cover 16, except that a single opening 17 for dissipation of heat, for instance, is open at the left end of the back cover 16 as viewed from the back of the refrigerator. Assuming that the front-to-back direction of the refrigerator is X-axis, the lateral direction is Y-axis and the vertical direction is Z-axis, the machine compartment has a one-dimensional duct structure in the direction of Y-axis. Thus, since the sectional area of the machine compartment 10 in the X-Z plane is sufficiently small as compared with the wavelength of the compressor noise to be reduced, the compressor noise is a one-dimensional plane progression wave in the direction of Y-axis. Specifically, when the dimension (duct length) of the machine compartment 10 in the direction of Y-axis is 640 mm or 880 mm and the dimension in the X and Z directions is about 250 mm, for instance, the acoustic mode prevails only in Y-direction at frequencies less than 800 Hz so that the machine compartment 10 may be regarded as a one-dimensional duct in Y-direction. Furthermore, the internal wall of the machine compartment 10 is clad with a sound absorbent, which is a soft tape, so as to prevent release of high-frequency noise not less than 800 Hz. Therefore, the frequencies of noise to be cancelled in the active noise attenuation system according to this embodiment are not less than 100 Hz but less than 800 Hz.

The reference numeral 20 indicates a compressor which is a main source of noise. This compressor 20 is rigidly secured to the bottom plate 15 at the right-hand end as viewed in FIG. 1. The compressor 20 is a rotary compressor having a cylindrical body, the right-hand part of which constitutes a motor segment 21 while the left-hand side constitutes a mechanical segment 22. Disposed at the end face of the motor segment 21 is a cluster unit 23, while a suction pipe 24 is connected to the end face of the mechanical segment 22.

Figure 23:
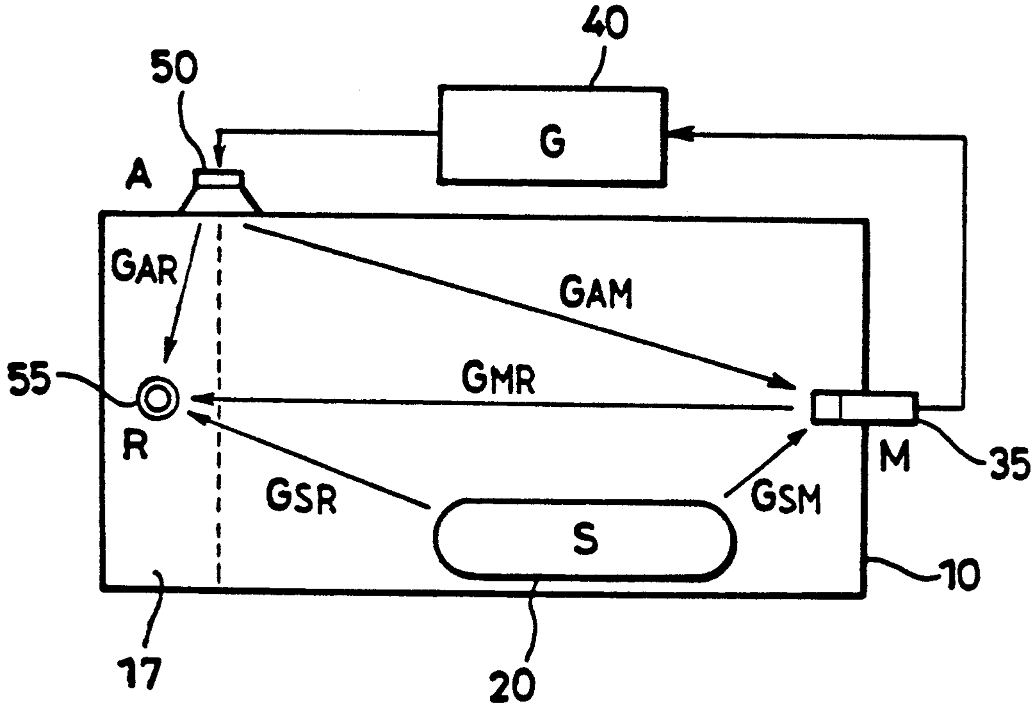
FIG. 23 (PRIOR ART)
FIG. 23 is a schematic view showing the prior art active noise attenuation system in the low-noise refrigerator.

The reference numeral 30 indicates a vibration pickup attached to the base of the suction pipe 24. This vibration pickup 30 takes the place of the microphone 35 shown in FIG. 23 illustrating the prior art system, and the vibrations of the compressor 20 are detected by this pickup 30. The vibration pickup 30 can be rather easily secured to the suction pipe 24 by means of a band.

The reference numeral 40 indicates a control circuit for processing output signals from the vibration pickup 30. This control circuit 40 is a cascade circuit comprising a low-pass filter 41, an A/D converter 42, an FIR filter 43 and a D/A converter 44. The low-pass filter 41 cuts high frequency signals in excess of one-half of the sampling frequency of the A/D converter 42 in order to preclude arising error. The A/D converter 42 converts an analog signal coming through the low-pass filter 41 to a digital signal so that it can be processed by the FIR filter 43. The FIR filter 43 convolutes the digital input signal and prepares a necessary output signal. The D/A converter 44 converts the digital signal from the FIR filter 43 to an analog signal and outputs it.

The reference numeral 50 is a noise attenuation speaker 50 connected to the output side of the D/A converter 44 of the control circuit 40. This speaker 50 is disposed to face the opening 17 at the left-hand end of the inclined front plate 14 as depicted. The controlling sound from this speaker 50 cancels the compressor noise which is to emerge from the machine compartment opening 17. When the upper limit to the noise attenuation frequencies is 800 Hz as aforesaid, the sampling frequency is preferably as high as possible over 1.4 KHz. The preferred sampling frequency is 6.4 KHz when the duct length is 640 mm, and it is 12.8 KHz for 880 mm.

Figure 2:
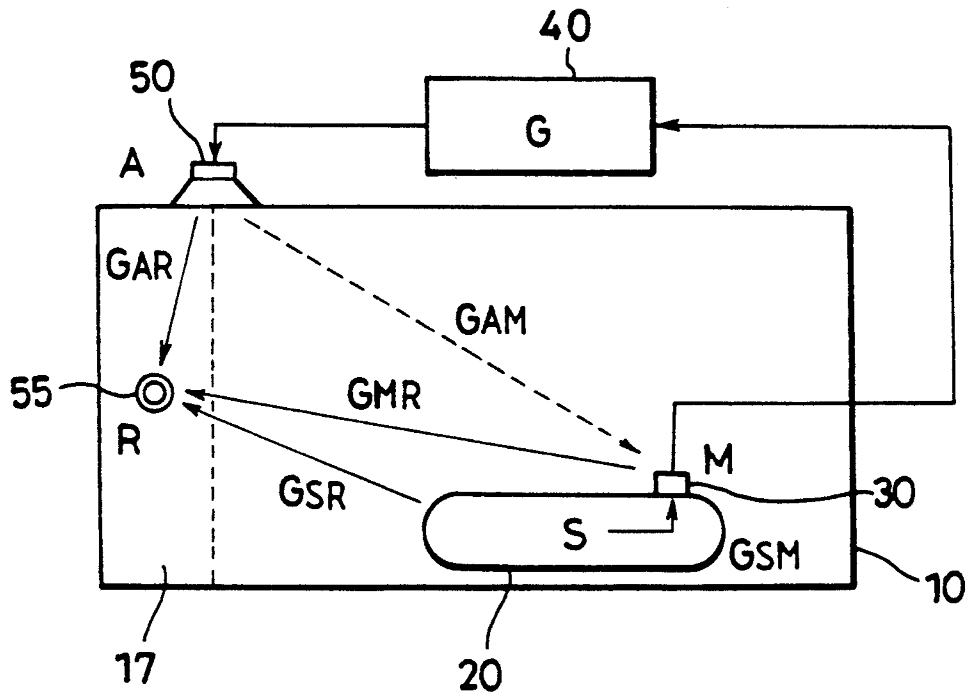

FIG. 2 is a schematic view showing the refrigerator active noise attenuation system described above.

The vibration pickup 30 substitutes the microphone 35 shown in FIG. 23 which illustrates the prior art noise attenuation system. Thus, in order to verify how the compressor noise can be attenuated by taking advantage of a correlation between the noise and vibration of the compressor 20, the following experiment was carried out (cf. FIGS. 3 and 4).

Figure 3:
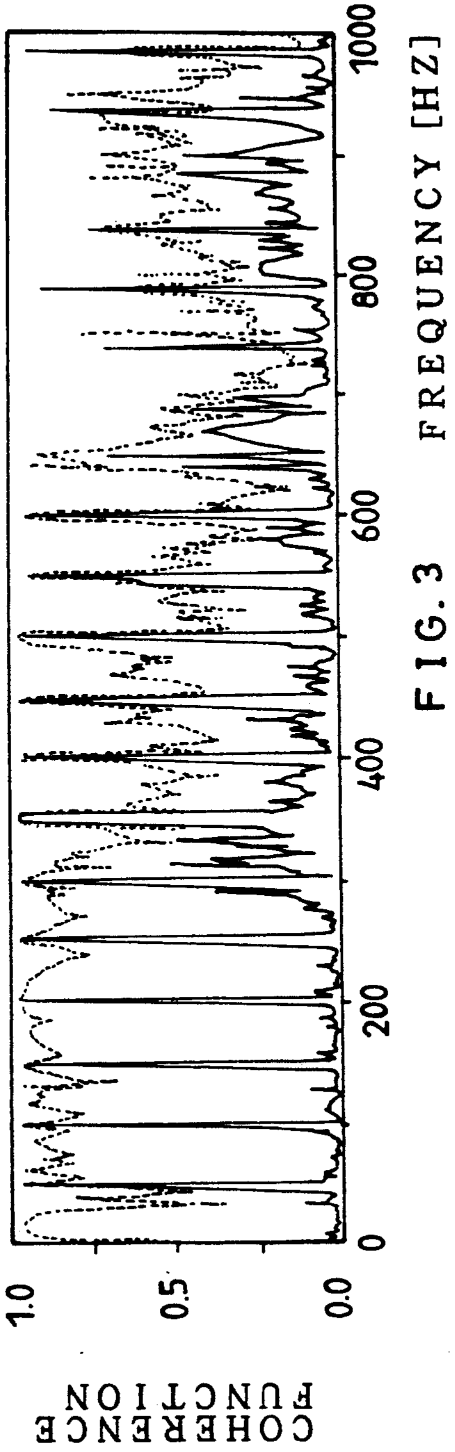
Figure 4:
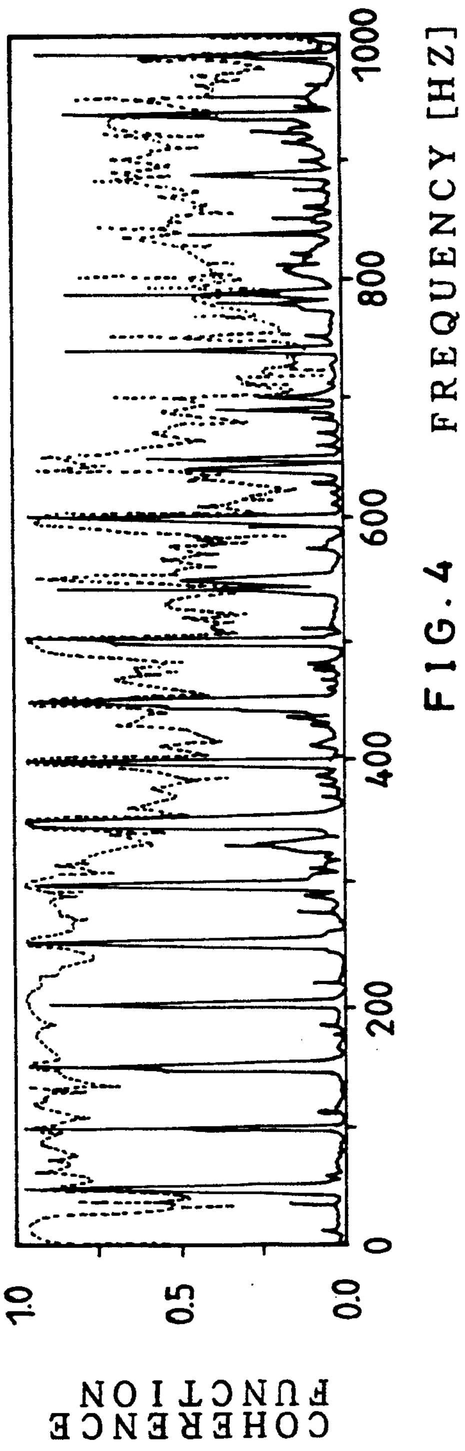

FIG. 3 is a diagram showing the coherence function between the vibration in X-direction of the compressor 20 as measured on the suction pipe 24 and the compressor noise detected by the microphone, and FIG. 4 is a diagram showing the coherence function between the vibration in Z-direction of the compressor 20 as similarly measured on the suction pipe 24 and the compressor noise. These coherence functions were determined with a two-channel FFT analyzer and are shown in the broken lines in the respective diagrams, where the solid lines represent the coherence functions between microphones.

As apparent from these diagrams, there is a good correlation between the vibration and the noise of the compressor 20. Thus, in constructing a noise attenuation system, measurement of vibrations at the suction pipe 24 can be used instead of detection of compressor noise S. Moreover, when the vibration pickup 30 is employed, the acoustic transfer function $G_{AM}$ between the speaker and the pickup is reduced to 0 (the following equation) as indicated in FIG. 2.

$$G_{AM}=0 \quad (8)$$

Substituting (8) into the equation (6) gives a very simplified expression (9).

$$G=-G_{MR}/G_{AR} \quad (9)$$

where $G_{MR}$ is the transfer function ratio of $G_{SR}$ to $G_{SM}$ which is given by the equation (7) which appears above.

When these equations (9) and (7) are used, just as in the case illustrated in FIG. 23, the transfer function G for the control circuit 40 which is necessary for reducing the sound R measured at the opening 17 by the evaluation microphone 55 to 0 can be found by determining the transfer function ratio $G_{MR}$ even if the compressor noise S is an unknown quantity. However, since the noise from the compressor 20 has a discrete spectrum composed of sounds of rotation and electromagnetic sounds, it is advisable to use only the transfer functions relevant to the number of revolutions of the compressor 20 and its high harmonics and those of the source frequency and its high harmonics as effective data and perform a linear interpolation.

When the transfer function G thus determined is previously applied to the control circuit 40, a controlling sound A corresponding to compressor noise S is outputted from the speaker 50 so as to attenuate the noise S at the machine compartment opening 17. Consequently, a noise reduction of, for example, not less than 5 dB can be accomplished. Furthermore, since the compressor noise S is only indirectly measured by the vibration pickup 30, there is no need for concern about howling due to the controlling sound A even if the output level of the speaker 50 is increased, nor is there an interference from sounds other than compressor noise, e.g. the noise of the fan and the external sound.

Since, as explained above, the low-noise refrigerator according to this embodiment is such that the vibrations of the compressor 20 are picked up by a vibration pickup 30 mounted on the base of the suction pipe 24 connected to the compressor 20, the thermal aging of the vibration pickup 30 is precluded so that erratic actions of the noise attenuation system S are inhibited.

The second embodiment of the present invention will now be described below, reference being had to FIGS. 5 through 7.

Figure 5:
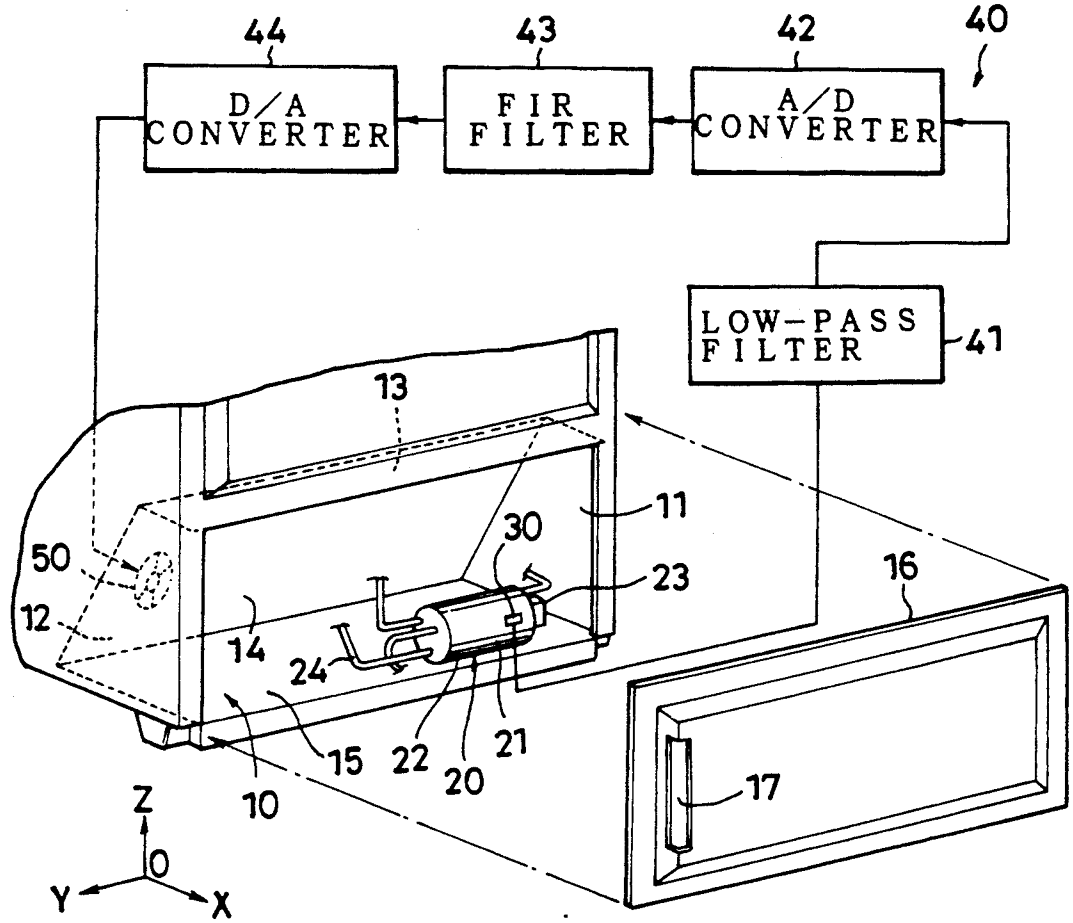

FIG. 5 is a disassembled perspective view showing the lowermost part at the back of a low-noise refrigerator according to this embodiment.

In this second embodiment, a compressor 20 is disposed in a machine compartment as far as possible from an opening 17 where the noise is radiated out and a speaker 50 as a noise-attenuating sound generator is disposed in the proximity of this opening 17. Furthermore, a vibration pickup 30 is mounted on the circumferential wall of a motor segment 21 so that the vibrations of the compressor 20 may be detected by this pickup 30.

Figure 6:
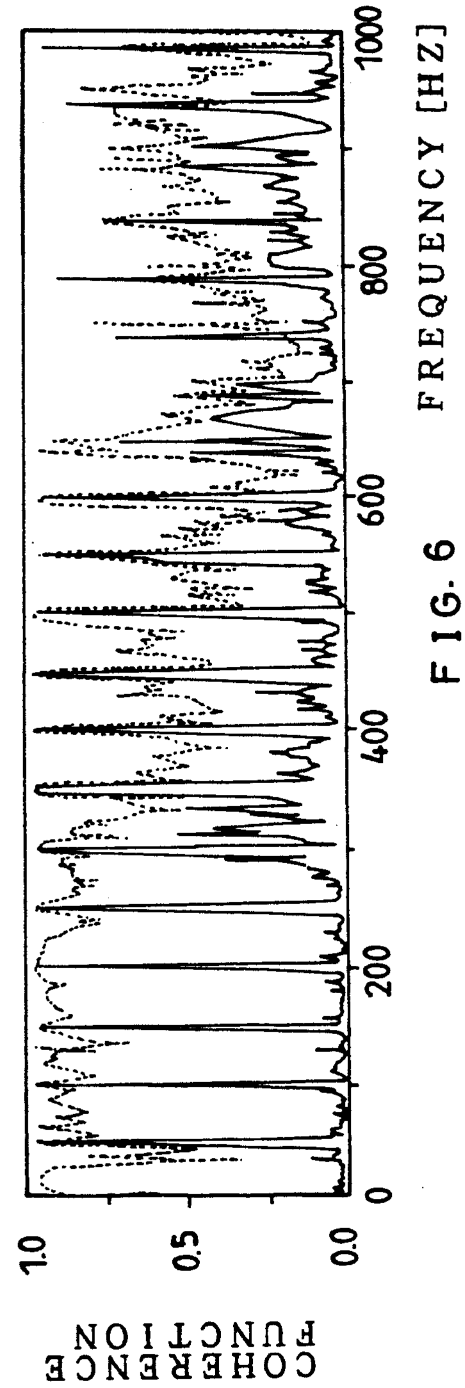
Figure 7:
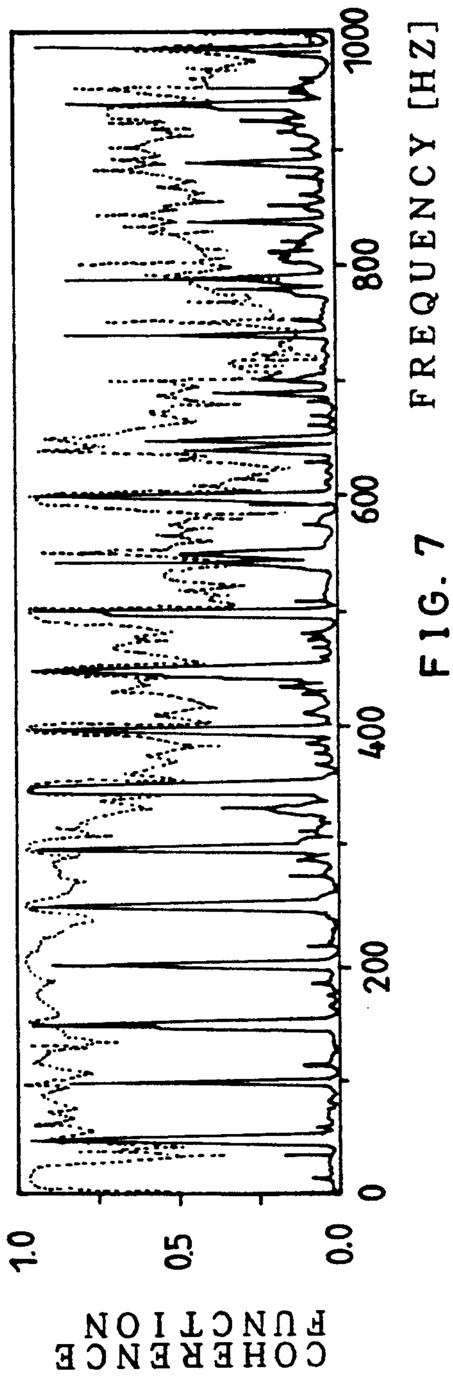

FIGS. 6 and 7 are diagrams showing the coherence functions between the vibrations of the compressor 20 as measured at different positions on the motor segment 21 of the compressor 20 and the compressor noises detected by the microphone. As these diagrams indicate, there is a good correlation between the vibration of the compressor 20 and the compressor noise. Stated differently, measurement of compressor vibrations can be successfully used in lieu of detection of compressor noise S.

When the transfer function G found by using equations (7) and (9) has been applied to the control circuit 40, a controlling sound A corresponding to compressor noise S can be outputted from the speaker 50 to cancel the noise S at the machine compartment opening 17, thus achieving a noise reduction of, for example, not less than 5 dB.

The series of actions, namely picking up the compressor vibrations with the pickup 30, processing the vibrations into noise attenuation signals in the control circuit 40, inputting the signals into the speaker 50, causing the speaker 50 to emit a controlling sound A and the sound A to reach the machine compartment opening 17, must be completed by the time when the noise wave radiated from the compressor 20 arrives at the opening 17. Therefore, in the present embodiment, a sufficient lead time is allotted to processing in the control circuit 40 by disposing the compressor 20 as far as possible from the machine compartment opening 17 and the noise attenuation speaker 50 in the neighborhood of the opening 17.

The third embodiment of the present invention will now be described, referring to FIGS. 8 through 14.

Figure 8:
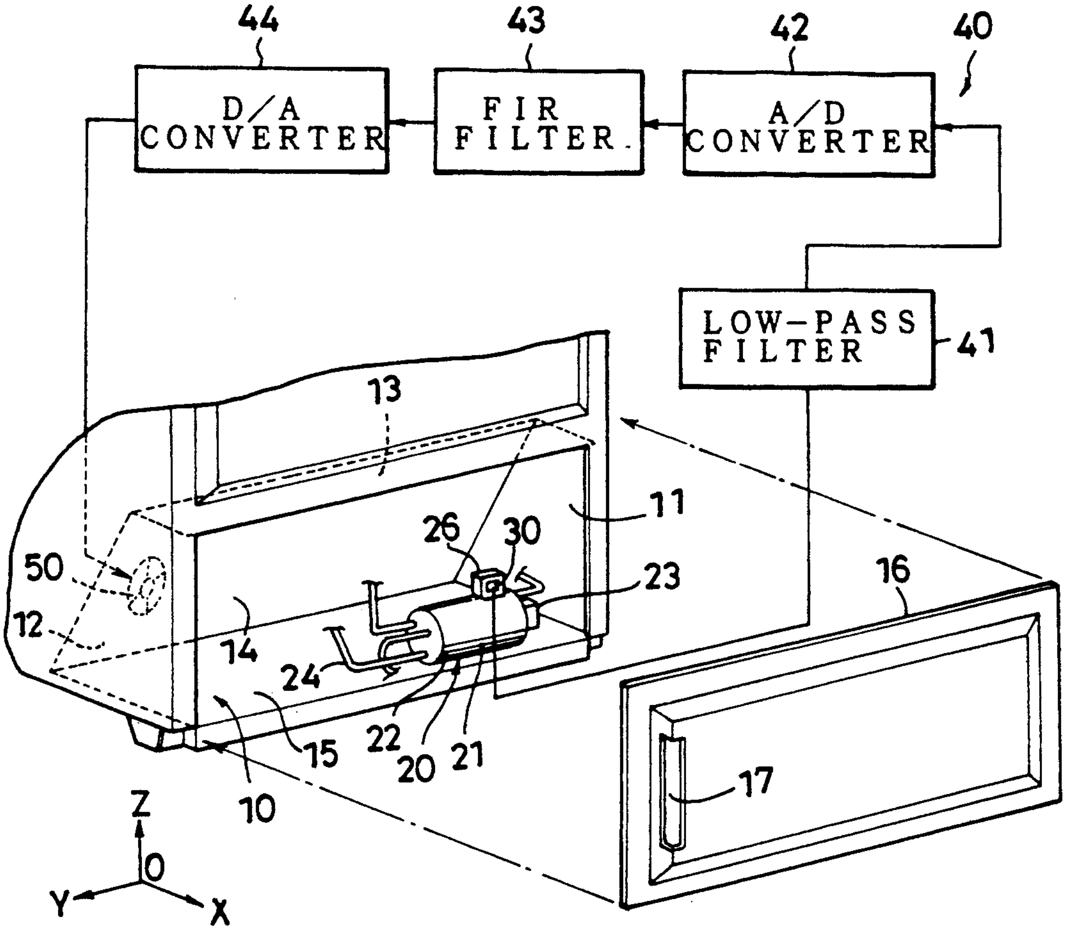

FIG. 8 is a disassembled perspective view showing the lowermost part at the back of a low-noise refrigerator according to this embodiment.

In the refrigerator, a plate-like jig 26 extending in the generator direction, i.e. Y-axis direction, is mounted on the circumferential surface of a rotary compressor 20 and a vibration pickup 30 is then mounted on the jig 26 the normal of which coincides with the X-axis so that the vibrations in the tangential direction of the compressor body are detected by the pickup 30.

Figure 10:
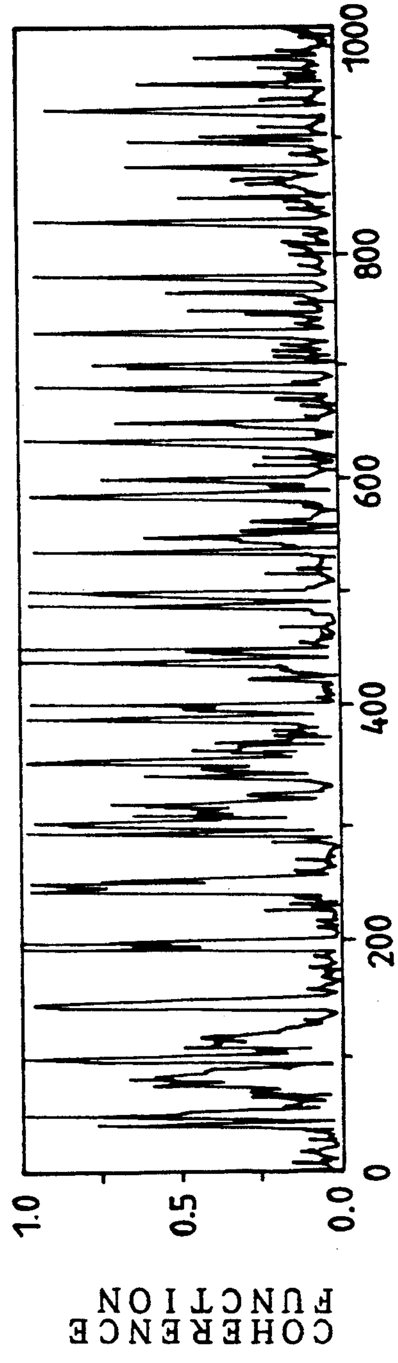

FIG. 10 is a diagram showing the coherence function, as measured with a two-channel FFT analyzer, between the tangential vibration of the rotary compressor body as detected by said vibration pickup 30 and the compressor noise detected by a microphone. As shown, there is a good correlation between the tangential vibration of the compressor body and the compressor noise S. Thus, in constructing a noise attenuation system, measurement of the vibrations of the compressor body in the tangential direction can be successfully utilized in lieu of the detection of compressor noise S.

Figure 9:
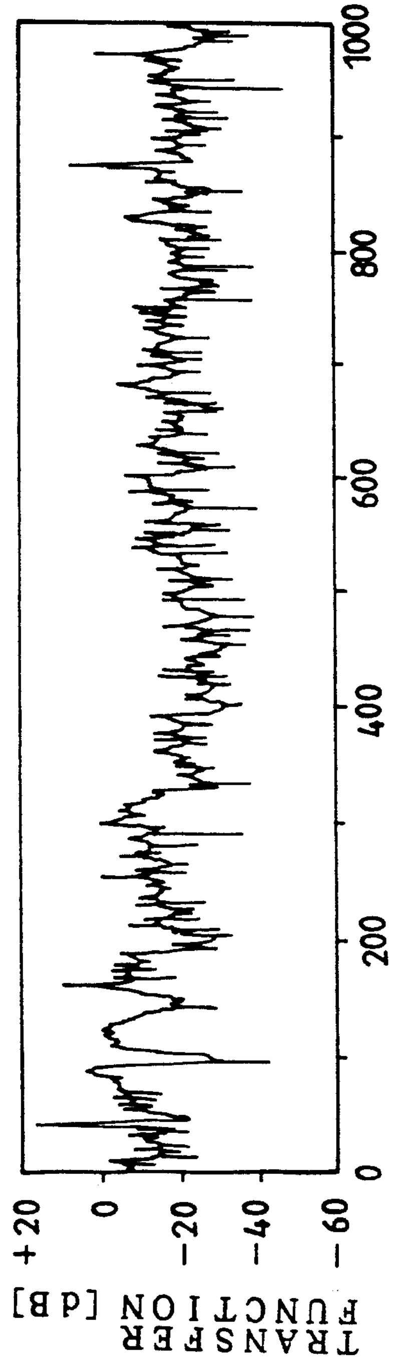
Figure 11:
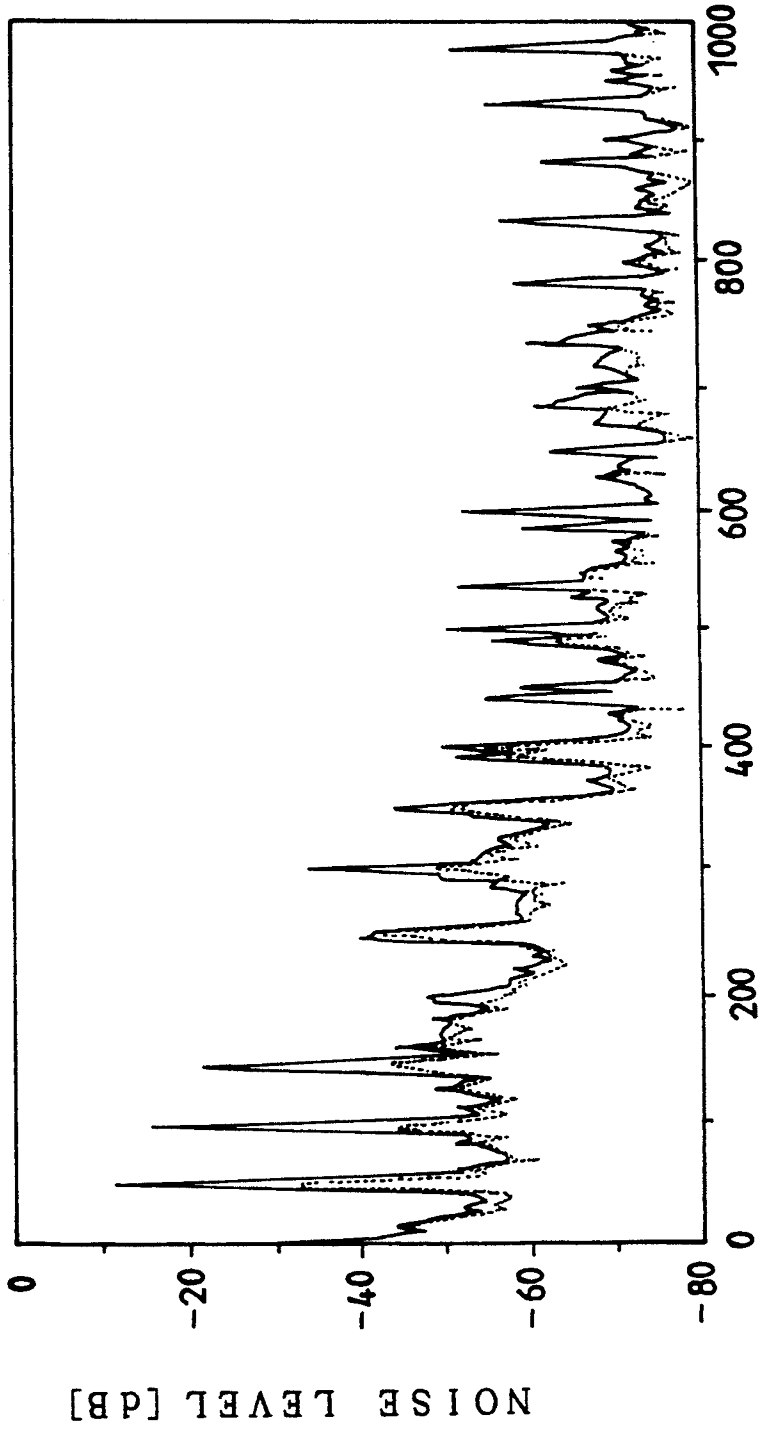

FIG. 9 shows an exemplary noise-attenuating transfer function G calculated by means of equations (7) and (9). When this transfer function G is previously applied to the control circuit 40, a controlling sound A corresponding to compressor noise S can be outputted from a speaker 50 to cancel this noise S at the machine compartment opening 17. The noise-reducing effect of this active noise attenuation system is shown in FIG. 11, in which the solid line represents the noise level prior to noise cancellation and the broken line represents the noise level after noise cancellation. As shown, a noise reduction of approximately 10 dB can be achieved in the present embodiment.

Figure 12:
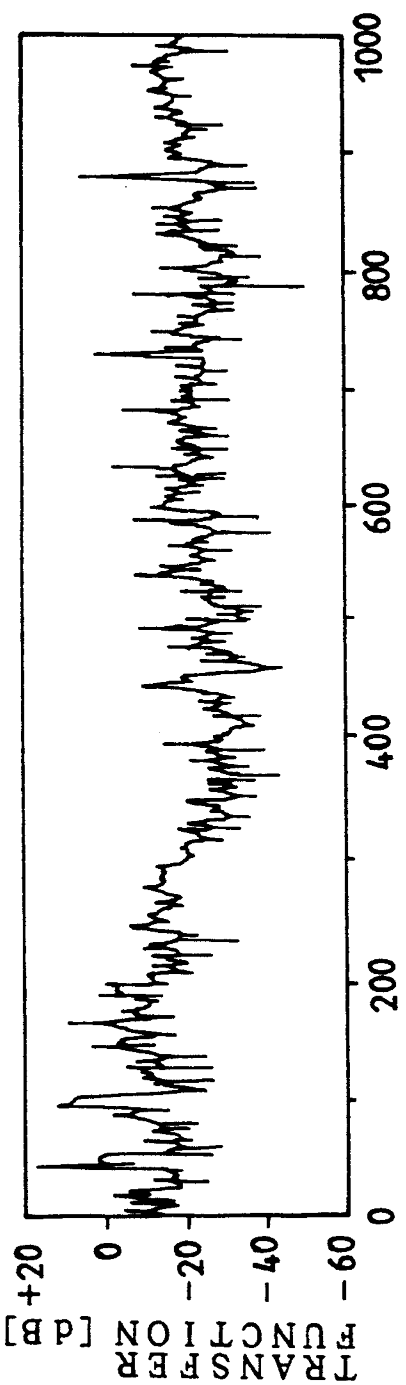
Figure 13:
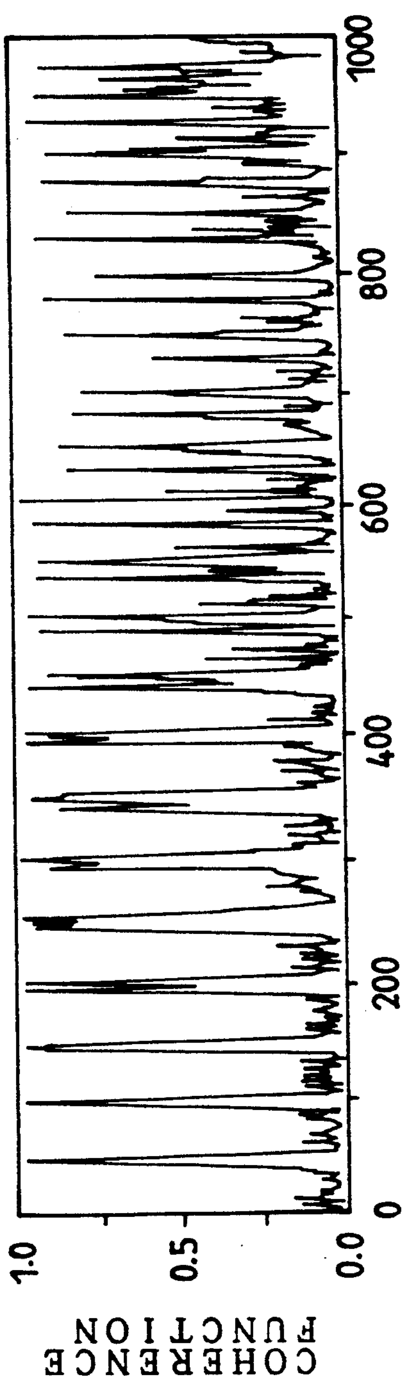
Figure 14:
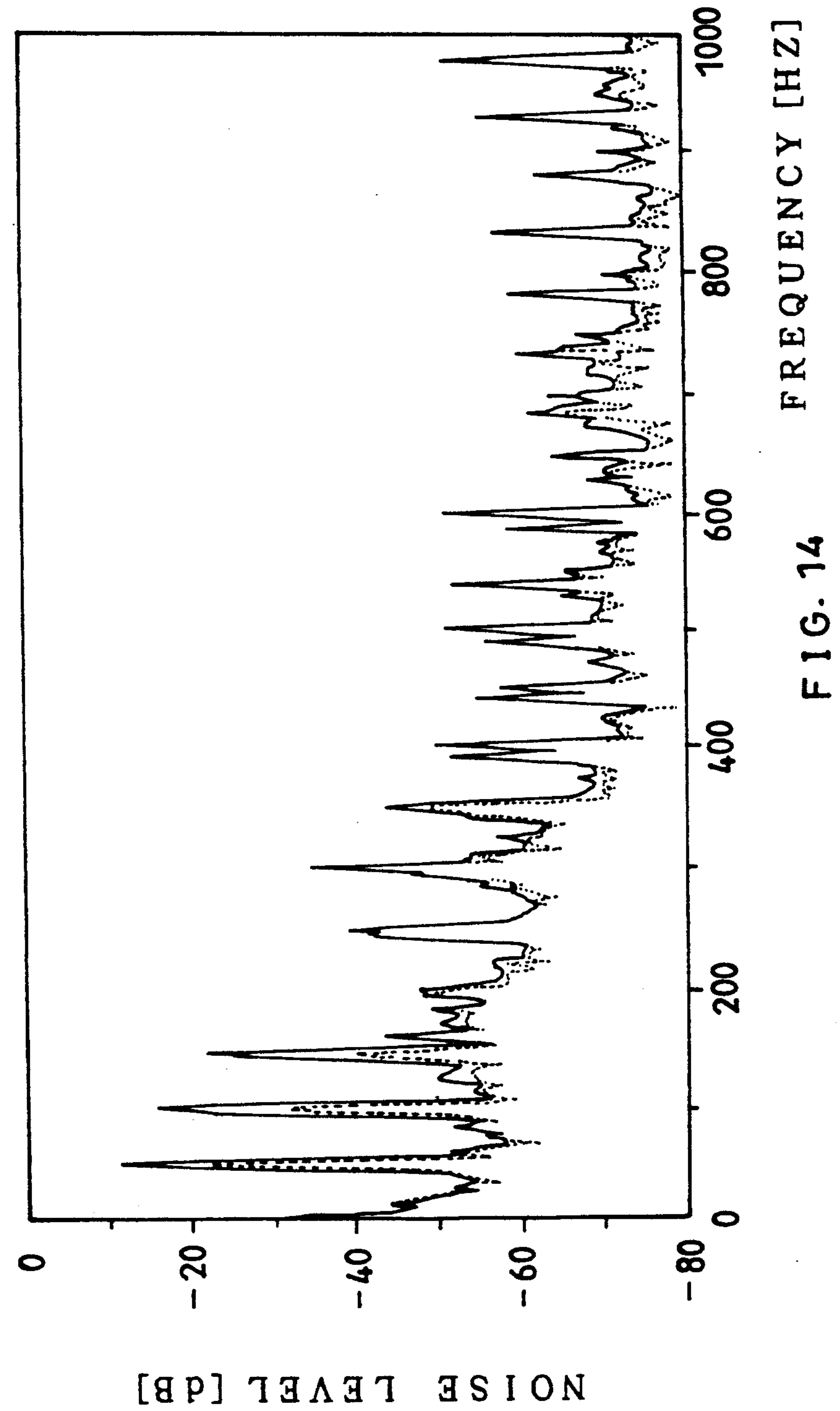

FIGS. 12 through 14 show the function and effect of the system in the detection of vibrations of the compressor body in the normal direction. These diagrams correspond to FIGS. 9 through 11. It is apparent that, in this system, the sensitivity of detection of vibrations is so low that a noise reduction of only about 7 dB can be obtained.

Thus, since the vibration pickup in the low-noise refrigerator according to this embodiment picks up the tangential vibrations instead of the normal vibrations of the compressor body, it can detect the sound of rotation of the rotary compressor with higher sensitivity.

Figure 16:
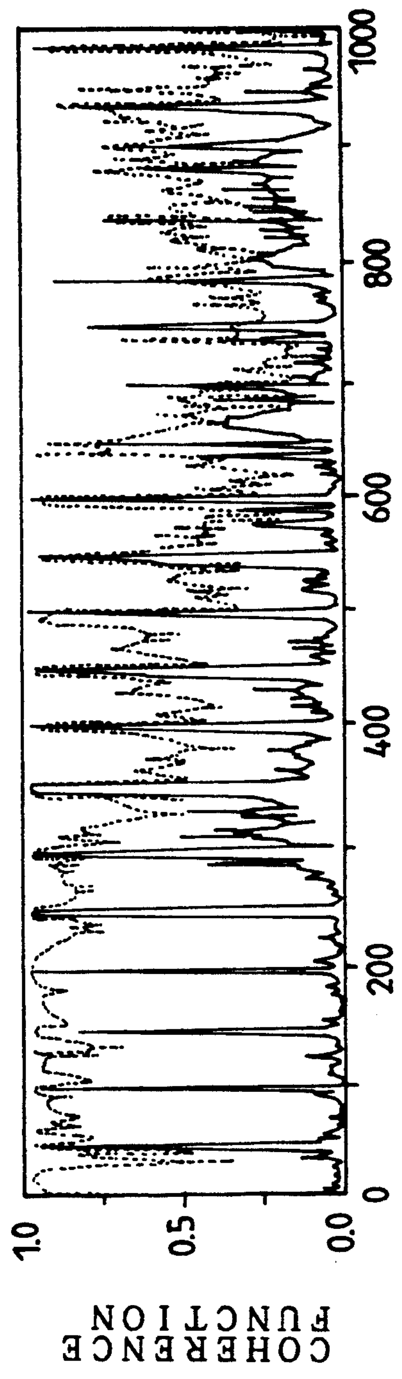
Figure 17:
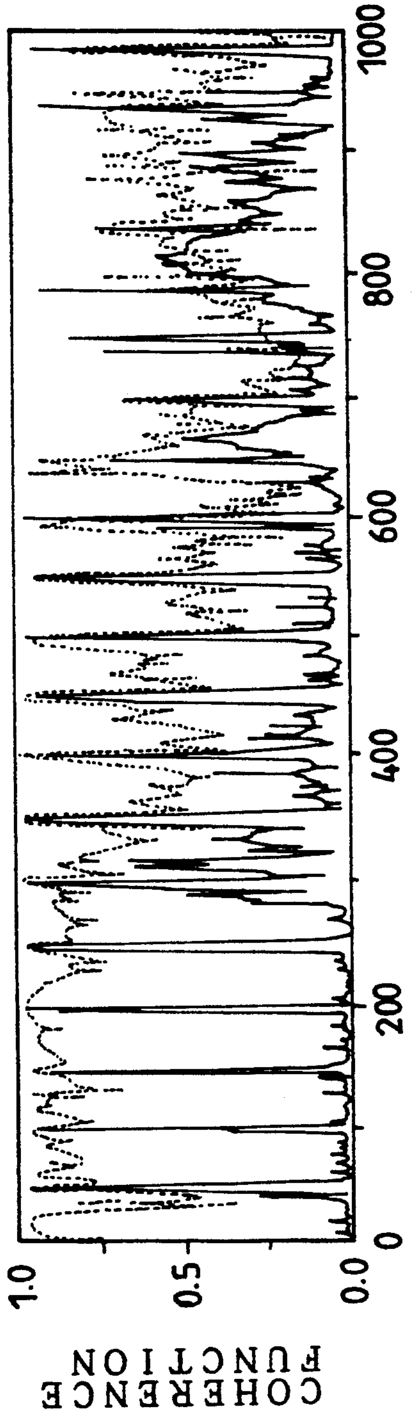

The fourth embodiment of the present invention will now be described with reference to FIGS. 15 through 17.

In this embodiment, the same devices as those described for the low-noise refrigerator of the first embodiment (FIG. 5) are employed.

In this fourth embodiment, the vibration pickup 30 is mounted on the circumferential surface of the motor segment 21 for detection of the vibrations of the compressor 20.

Figure 15:
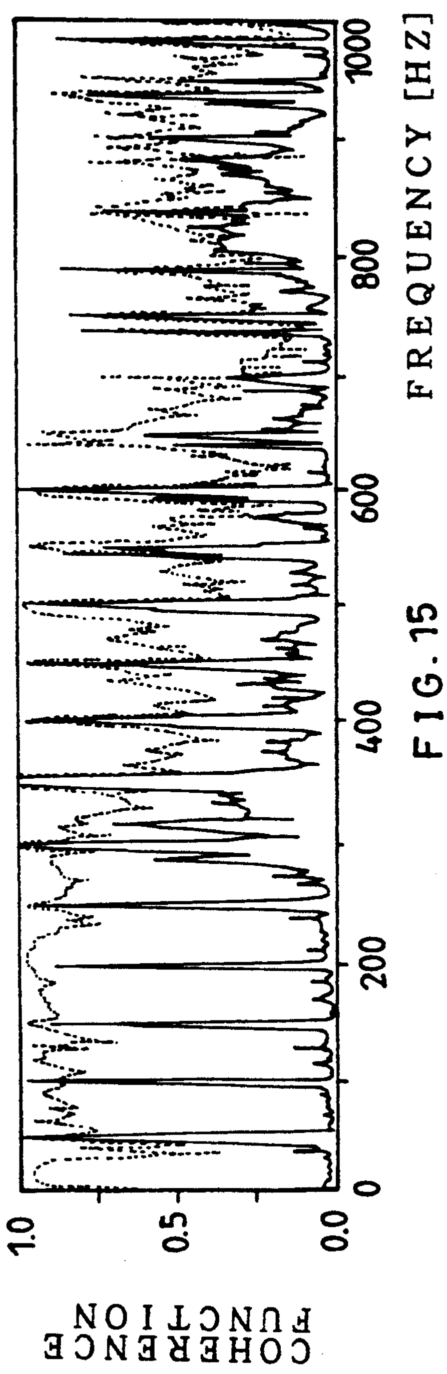

FIGS. 15 through 7 are diagrams showing the coherence functions between the compressor vibration measured at three respective positions on the motor segment 21 of the compressor 20 and the compressor noise. These coherence functions were determined with a two-channel FFT analyzer, and are represented by broken lines in FIG. 3. The solid line in the diagram represents the coherence function between the microphones. As apparent from FIG. 3, there is a good correlation between the vibration and noise of the compressor 20. Thus, in constructing a noise attenuation system, measurement of vibrations of the motor segment 21 of the compressor can be used in lieu of the detection of compressor noise S.

When the transfer function G calculated by means of equations (7) and (9) are previously fed to the control circuit 40, a controlling sound A corresponding to compressor noise S can be outputted from the speaker 50 so as to cancel the noise S at the machine compartment opening 17, whereby a noise reduction of, for example, not less than 5 dB can be accomplished.

The fifth embodiment of the present invention will now be described, referring to FIGS. 18 through 20.

Figure 18:
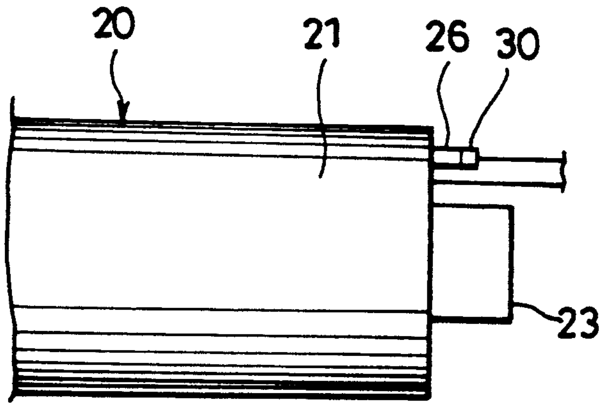

FIG. 18 is a side elevation view of a compressor 20 showing the mounting position of a vibration pickup 30 in a low-noise refrigerator according to the fifth embodiment of the invention.

Referring to the compressor 20, since the end face of its motor segment, i.e. the end face of a cluster part 23 of the compressor body, is not only close to the build-in motor but presents a flat surface, it can be opportunely utilized as the location for a vibration pickup 30. In this embodiment, a bolt 26 is welded to the end face of this motor segment 21 and the vibration pickup 30 is secured to this bolt 26. In this arrangement, the vibration pickup 30 can be easily and securely mounted without chances of installation error. The advantage of plane contact between the compressor 20 and the vibration pickup 30 can also be implemented by mounting a planar vibration pickup 30 directly on the end face of the motor segment 21 without employing the bolt 26.

Figure 19:
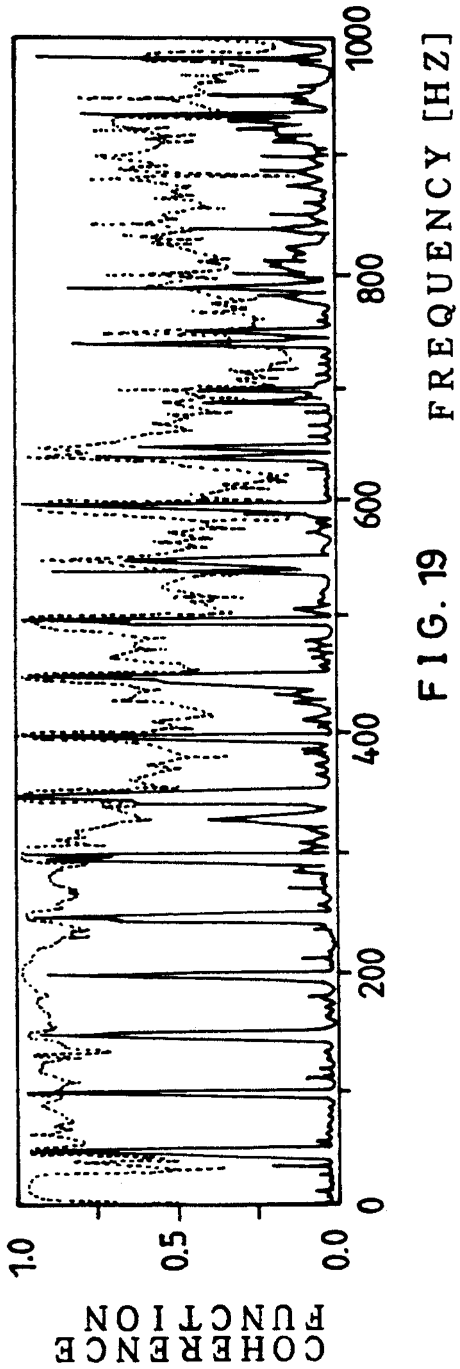
Figure 20:
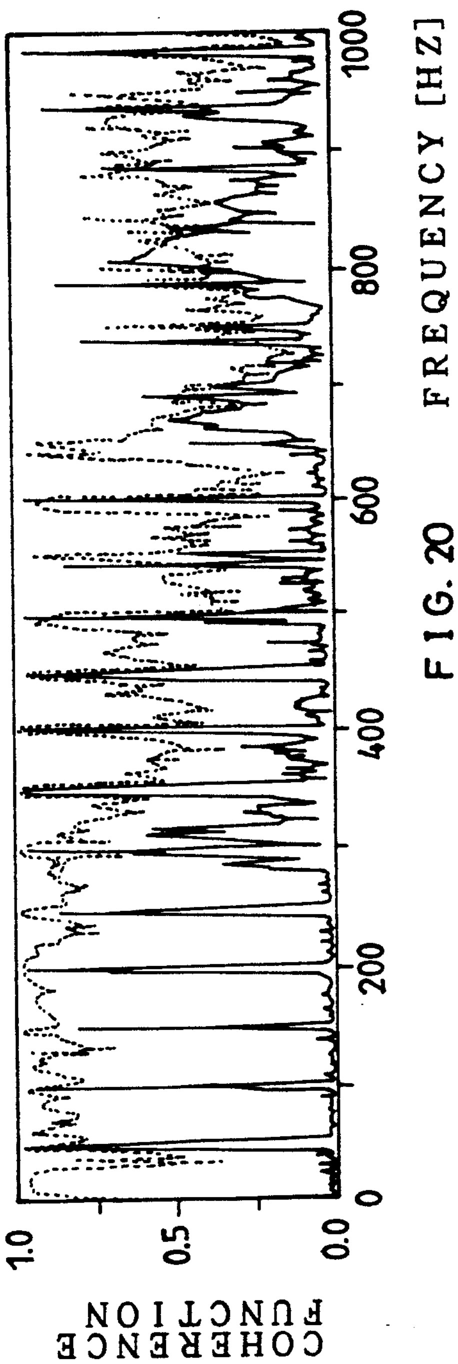

FIG. 19 is a diagram showing the coherence function between the compressor vibration in X-direction as measured at the mounting position of the vibration pickup shown in FIG. 18 and the compressor noise, and FIG. 20 is diagram showing the coherence function between the compressor vibration in Y-direction as measured on the circumferential surface of the motor segment 21 and the compressor noise. These coherence function values are represented by broken lines in the respective diagrams. The solid lines in these diagrams represent the coherence function between microphones. As shown, there is a good relation between the vibration and noise of the compressor 20. Thus, in this case, too, measurement of the vibrations of the motor segment 21 of the compressor can be used in lieu of the detection of compressor noise S.

The low-noise refrigerators according to the fourth and fifth embodiments each employs an active noise attenuation system by which the compressor noise can be indirectly and efficiently measured via a vibration pickup mounted on the compressor motor segment which is located close to the vibration source. Consequently, there is no cause for concern about howling even if the output of the noise-attenuating sound generator is increased, nor is there an interference from the noise of the compressor cooling fan and the external noise.

Figure 21:
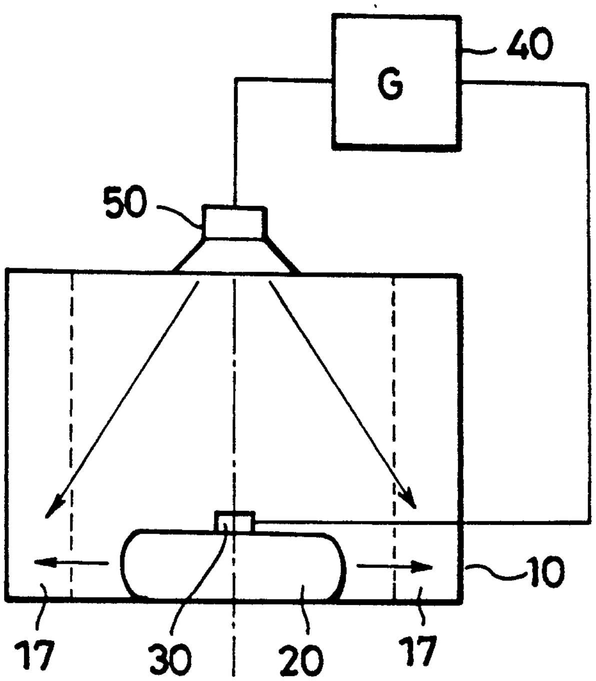
FIG. 21 is a schematic view showing an active noise attenuation system in the low-noise refrigerator.

The sixth embodiment of the present invention will now be described below, reference being had to FIG. 21 which schematically illustrates an active noise attenuation system for the low-noise refrigerator.

In this sixth embodiment, a machine compartment 10 is provided with two openings 17, 17 at both ends and a rotary compressor 20 and a noise-attenuating speaker 50 are installed in a central zone. A vibration pickup 30 is mounted on the circumferential surface of the compressor 20. This machine compartment 10 is designed to be symmetrical about its center line on which the noise-source compressor 20, noise-attenuating speaker 50 and vibration pickup 30 are disposed.

In the above arrangement, the transfer function from the compressor 20 to the openings 17, 17 can be made equal to the transfer function from the speaker 50 to the openings 17, 17 so that two openings 17, 17 can be dealt with a single noise attenuation system. Particularly in the first through the fifth embodiments, the dimension of opening 17 must be reduced to 17 cm or less in order that the noise of frequencies below 1 KH may be cancelled, with the result that the dissipation of heat from the compressor 20 may not be sufficient. In this embodiment, however, a couple of openings can be provided to insure a sufficient dissipation of compressor heat.

Figure 22:
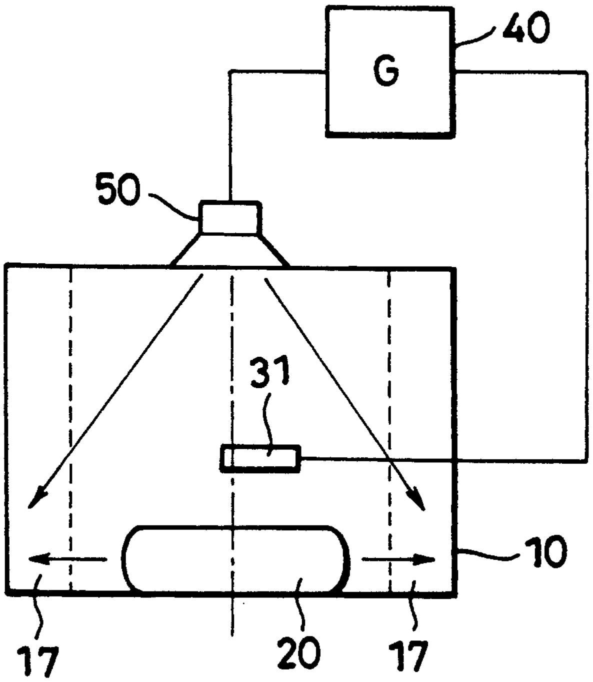
FIG. 22 is a schematic view showing an active noise attenuation system similar to that shown in Fig. except that a microphone is used in lieu of the vibration pickup.

It should be understood that, in connection with this embodiment, the use of a microphone 31 in lieu of the vibration pickup 30 as means for collecting noise source signals from the compressor 20 as shown in FIG. 22 results in a similar noise attenuation effect.

While, in the first through the sixth embodiments, real time control is executed by interposing an FIR filter 43 in the control circuit 40, delayed control with a delay time equivalent to one cycle can also be executed. Furthermore, adaptive control involving automatic modification of the noise-attenuating transfer function G which adjusts for deviations in transfer function G due to aging and solid differences can also be implemented.

It should be understood that the present invention can be used for silencing the noise of any machinery installed in a machine compartment having an opening for heat dissipation, this being not limited to the refrigerator.

What is claimed is:

1. A silencer attenuating noise from a noise source requiring ventilation, the silencer comprising:
   - a machine compartment with a one-dimensional duct configuration whose sectional dimension is sufficiently small in comparison with wavelength of the noise to be reduced, the noise source being disposed therein;
   - an opening for dissipation of heat as disposed in a wall of the machine compartment and opening in a direction generally perpendicular to the direction of advance of the noise within the machine compartment;
   - a vibration pickup means for detecting vibrations of the noise source, the vibration pickup means being attached to the noise source;
   - a control circuit for processing signal outputs of the vibration pickup means; and
   - a sound generator, such as a speaker, which is driven by output signals from the control circuit to output a controlling sound in the machine compartment and to cancel thereby the noise which is about to emerge from the opening.

2. A silencer according to claim 1, wherein the noise source is a compressor constituting a refrigerating cycle.

3. A silencer according to claim 2, wherein
   - the noise source additionally includes a suction pipe having a portion proximate to the compressor, and
   - the vibration pickup means is mounted on the portion of the suction pipe proximate to the compressor.

4. A silencer according to claim 2, wherein the compressor is disposed as far distant as possible from the opening.

5. A silencer according to claim 2, wherein
   - the compressor includes a cylindrical body, and
   - the vibration pickup means is mounted on the cylindrical body.

6. A silencer according to claim 5, wherein the vibration pickup means is for detecting vibrations of the compressor in a direction tangential to the cylindrical body.

7. A silencer according to claim 2, wherein
   - the compressor includes a motor segment, and
   - the vibration pickup means is mounted on the motor segment.

8. A silencer according to claim 7, wherein
   - the motor segment includes an end face, and
   - the vibration pickup means is mounted on the end face.

9. A silencer according tot any one of claims 1, 2, 3, 4, 5, 7 or 8, wherein the control circuit includes a transfer function applying means for applying a noise-attenuation transfer function G to cause the sound generator, such as a speaker, to output a controlling sound corresponding to the noise of the noise source to thereby cancel the noise about to emerge from the opening with the controlling sound.

10. A silencer according to claim 13, wherein the transfer function applying means is for applying a transfer function G defined by:

$$G = -G_{MR}/G_{AR}$$

$$G_{MR} = G_{SR}/G_{SM}$$

where $G_{SR}$ is the acoustic transfer function between the noise source and the opening, $G_{AR}$ is the acoustic transfer function between the sound generator, such as a speaker, and the opening, and $G_{SM}$ is the transfer function between the noise source and the vibration pickup means.

11. A silencer attenuating a noise from a noise source to be ventilated, comprising:
   - a machine compartment with a one-dimensional duct configuration whose sectional dimension is sufficiently small in comparison with wavelength of the noise to be reduced;
   - a couple of openings for dissipation of heat as formed in opposed end portions of a wall of the machine compartment and opening in a direction generally perpendicular to the direction of advance of the noise in the machine compartment;
   - a compressor and other machinery as the noise source disposed in a central zone of the machine compartment;
   - a noise signal collecting means for detecting vibrations of the noise source;

a control circuit for processing output signals from the noise source signal collecting means, and a sound generator, such as a speaker, which is disposed in a central zone within the machine compartment and driven by output signals from the control circuit to output a controlling sound within the machine compartment and thereby cancels the machine noise which is about to emerge from the couple of openings.

12. A silencer according to claim 11 wherein the noise source signal collecting means includes a vibration pickup.

13. A silencer according to claims 11 or 12, wherein the control circuit includes a transfer function applying means for applying a noise-attenuation transfer function G to cause the sound generator, such as a speaker, to output a controlling sound corresponding to the noise of the noise source to thereby cancel the noise about to emerge from the couple of openings with the controlling sound.

14. A silencer according to claim 13, wherein the transfer function applying means is for applying a transfer function G defined by:

$$G=-G_{MR}/G_{AR}$$

$$G_{MR}/G_{Sm}$$

where $G_{SR}$ is the acoustic transfer function between the noise source and the couple of openings, $G_{AR}$ is the acoustic transfer function between the sound generator, such as a speaker, and the couple of openings, and $G_{SM}$ is the transfer function between the the noise source and the noise signal collecting means.

* * * * *